(12) United States Patent
Kitagawa et al.

(10) Patent No.: US 7,898,256 B2
(45) Date of Patent: Mar. 1, 2011

(54) NUCLEAR MAGNETIC RESONANCE MEASUREMENT APPARATUS AND MEASURING METHOD USING THE SAME

(75) Inventors: Isao Kitagawa, Kokubunji (JP); Michiya Okada, Mito (JP); Kazuo Saitoh, Kodaira (JP)

(73) Assignee: Hitachi, Ltd., Tokyo (JP)

( * ) Notice: Subject to any disclaimer, the term of this patent is extended or adjusted under 35 U.S.C. 154(b) by 187 days.

(21) Appl. No.: 12/371,963

(22) Filed: Feb. 17, 2009

(65) Prior Publication Data

US 2009/0212776 A1 Aug. 27, 2009

(30) Foreign Application Priority Data

Feb. 22, 2008 (JP) ............................. 2008-041127

(51) Int. Cl.
*G01V 3/00* (2006.01)
(52) U.S. Cl. ...................................... 324/318; 324/321
(58) Field of Classification Search ......... 324/300–322; 600/407–445
See application file for complete search history.

(56) References Cited

U.S. PATENT DOCUMENTS

| | | | | |
|---|---|---|---|---|
| 5,397,989 A | * | 3/1995 | Spraul et al. | ................. 324/321 |
| 5,698,409 A | * | 12/1997 | O'Neill | ..................... 435/7.23 |
| 5,965,448 A | * | 10/1999 | Katou et al. | .................. 436/52 |
| 7,449,890 B2 | * | 11/2008 | Kitagawa et al. | ............. 324/321 |
| 7,463,032 B2 | * | 12/2008 | Takahashi et al. | ........... 324/321 |
| 7,492,157 B2 | * | 2/2009 | Kitagawa et al. | ............. 324/318 |
| 7,597,790 B2 | * | 10/2009 | Neyer et al. | .................. 204/450 |
| 7,719,273 B2 | * | 5/2010 | Kitagawa et al. | ............. 324/307 |

FOREIGN PATENT DOCUMENTS

| | | |
|---|---|---|
| JP | 2003-510608 | 3/2003 |
| JP | 2004-534958 | 11/2004 |
| JP | 2007-315826 | 12/2007 |

* cited by examiner

*Primary Examiner*—Brij B Shrivastav
(74) *Attorney, Agent, or Firm*—Antonelli, Terry, Stout & Kraus, LLP.

(57) ABSTRACT

An NMR measurement apparatus adopts a circulation flow scheme using a sample solution containing a high molecular compound representing a measuring object and a low molecular compound solution containing a low molecular compound representing a ligand. The measurement apparatus comprises a mixing filter 32 for mixing the sample solution and the low molecular compound solution, a separation filter 34 for performing separation therebetween, a flow channel 1 through which the sample solution drained out of the separation filter 34 is injected to the mixing filter 32, a flow channel 2 through which the low molecular compound solution drained out of the separation filter 34 is injected to the mixing filter 32, and a flow channel 3 through which the mixture solution drained out of the mixing filter 32 is injected to the separation filter 34 by way of a reservoir 10.

20 Claims, 7 Drawing Sheets ns and a nuclear magnetic resonance probe
NUCLEAR MAGNETIC RESONANCE MEASUREMENT APPARATUS AND MEASURING METHOD USING THE SAME

BACKGROUND OF THE INVENTION

The present invention relates to a nuclear magnetic resonance measurement apparatus and a measuring method using the same and more particularly, to a technique effectively applicable to the nuclear magnetic resonance measurement of a high molecular compound such as protein or macromolecule.

Such a molecule as protein functioning in a living body has a larger molecular weight in comparison with a low molecular compound of molecular weight 1000 or less used for medicine and the like and has characteristics of a high molecular compound. The high molecular compound typified by the protein functions molecularly in a solution and the molecular function is either hindered or promoted when the high molecular compound combines with a specified low molecular compound. The combination or interaction of the specified low molecular compound with the high molecular compound can be detected through many methods.

Especially, in the nuclear magnetic resonance measurement (hereinafter referred to as NMR measurement) capable of directly observing information about a molecular structure of the high molecular compound or the low molecular compound, not only the dissociation constant and reaction rate the high molecular compound and low molecular compound have can be evaluated from how the measuring spectrum changes with the compound concentration but also the interaction can be analyzed on the basis of the structure of the compound. JP-A-2003-510608 (Patent Document 1) describes a method of measuring the interaction between protein and low molecular compound through the NMR measurement.

Of the high molecular compounds used for the NMR measurement, the protein can be formed through a method of extracting it from a living body existing in the natural world, a method of extracting it from a mass developing system that takes advantage of, for example, colitis germs built in with a gene associated with formation of the target protein or a method of utilizing a non-cell developing system that develops a large amount of proteins without using living cells. Further, in some case, principal elements constituting the protein such as hydrogen, carbon and nitrogen are marked (hereinafter termed labeled) with isotope radioactive elements. Available in the labeling are a method of performing labeling by using the three elements of hydrogen, carbon and nitrogen constituting the protein in combination, a method of total marking for labeling all elements and a method of selective marking for labeling only atoms belonging to a specified amino acid residue. In any methods, the cost of labeling process is high.

Typically, the nuclear magnetic resonance measurement apparatus (hereinafter referred to as NMR measurement apparatus) comprises a magnet for generating a statistic magnetic field (Bo) and a nuclear magnetic resonance probe placed in a space inside the magnet. The nuclear magnetic resonance probe includes one or more coils adapted to apply an RF magnetic field ($B_1$) to a target sample and detect a reaction (response) the sample makes to the applied RF magnetic field.

The conventional nuclear magnetic resonance probe is sorted into a stationary sample probe and a flow-through probe. In the stationary sample probe, a method is adopted in which a sample is fed into a glass tube or an ampule (hereinafter referred to as a sample tube), the sample tube is set at a predetermined location in the NMR measurement apparatus and thereafter measurement is started.

In titration measurement using the conventional stationary sample probe, NMR measurement is carried out while titrating a low molecular compound with the help of a sample tube having an opening, so that how an NMR spectrum changes with an increase in concentration can be observed. But a sample solution is a mixture solution containing a high molecular compound, a low molecular compound representing a medicine effect evaluation target and other reagents and therefore, once the sample solution has reached a condition of containing the low molecular compound at a certain concentration, the NMR measurement is difficult to proceed by using that low molecular compound under a condition of lower concentration.

Further, because of the volume of the sample tube being small, as the titration of the low molecular compound proceeds and the volume of the total sample solution increases relatively, the concentration of the high molecular compound sample changes and besides the liquid level of the sample solution changes. In order to suppress these changes, the volume to be titrated needs to be reduced as far as possible in relation to the volume of the sample solution. But for reduction of the titration volume, the concentration of the low molecular compound is required to be increased. The concentration of a titration solution has, however, its upper limit that is determined by the solubility of the low molecular compound and in general, the solubility of substance differs remarkably with the kind of a solvent and the temperature.

As described above, in the adjustment of low molecular compound concentration through titration, the sample volume varies. The variation changes in its magnitude with the combination of low molecular compound and high molecular compound, the solvent and the temperature. The concentration change is unidirectional.

On the other hand, the conventional flow-through probe includes a sample inlet, a sample outlet and an internal tube extending between the inlet and the outlet. The internal tube contains a cell for holding a sample. A sample flows from the sample inlet to enter the cell through the internal tube. After measurement, the sample flows through the tube so as to be discarded externally of the probe.

The conventional flow-through probe has been used in combination with a robot-type sample conveyance system. In the system, samples adjusted for a plurality of measurement conditions need to be prepared in advance in a plurality of reservoirs. The sample is conveyed, via a unit capable of bringing out the sample, from a reservoir to a flow-through probe set in advance. JP-A-2004-534958 (Patent Document 2) describes the sample conveyance system.

In the combination of the conventional flow-through probe with the sample conveyance system, samples adjusted for the plurality of concentration conditions are required to be prepared in advance. Accordingly, high molecular compound solutions of predetermined concentrations are necessary correspondingly to the number of measurement conditions and high costs are required of the samples.

In the case of high molecular compound and low molecular compound for which the measurement condition range is unknown, the whole of measurement of function evaluation must be repeated until a preferable range of measurement conditions and the degree of changes in conditions are settled, raising a troublesome problem. JP-A-2007-315826 (Patent Document 3) describes a system capable of performing repetition of NMR measurement by utilizing a simplified circulation channel.

[Patent Document 1] JP-A-2003-510608
[Patent Document 2] JP-A-2004-534958
[Patent Document 3] JP-A-2007-315826

SUMMARY OF THE INVENTION

The present inventors have studied an NMR measurement apparatus as will be described below with reference to FIG. 7. The NMR measurement apparatus the present inventors have studied has, for execution of NMR measurements, a reservoir 10 for holding a mixture solution containing a high molecular compound such as protein representing an object to be measured and a low molecular compound representing a ligand, a magnet 20 of split type for applying a magnetic field to the mixture solution held in the reservoir 10, a nuclear magnetic resonance probe 24 attached to the reservoir 10 and a transmission/reception system 26 for storing NMR signals from the nuclear magnetic resonance probe 24.

The reservoir 10 has a drainage port 12 and an injection port 14 for the mixture solution and is connected to a sample conveyance pipe 1616 constituting a closed channel 5. Provided for the sample conveyance pipe 1616 are a syringe 90 for injecting a sample solution containing a high molecular compound and a syringe 80 for injecting a low molecular compound solution containing a low molecular compound. For example, the low molecular compound solution is first injected to the sample conveyance pipe 1616 from the syringe 80 and subsequently, the sample solution is injected to the sample conveyance pipe 1616 from the syringe 90 and they are caused by a circulating pump (not shown) to be circulated in form of a mixture solution through the channel 5.

The mixture solution circulated and hence uniformized stays in the reservoir 10 as a result of stoppage of its circulation and NMR measurement starts.

In the NMR measurement apparatus studied by the present inventors as above, however, when conducting the NMR measurement by changing the low molecular compound concentration, an NMR signal needs to be captured in advance under the condition that a high molecular compound is not injected with a view to examining a low molecular compound concentration and thereafter, the high molecular compound is injected under the same condition and NMR measurement of a mixture solution in the reservoir 10 repeats itself, thus requiring that the NMR measurement of the low molecular compound concentration be carried out in each phase of repetition.

An object of the present invention is to provide a technique for improving controllability of the NMR measurement apparatus.

The above and other objects and novel features of the present invention will become apparent from the description in the present specification and the accompanying drawings.

Of inventions disclosed in the present application, typical ones will be outlined briefly as follows.

An NMR measurement apparatus according to an embodiment of the present invention comprises a reservoir for holding a mixture solution containing a first compound (high molecular compound) and a second compound (low molecular compound), a magnet for applying a magnetic field to the mixture solution held in the reservoir, and a nuclear magnetic resonance probe attached to the reservoir, wherein a circulation-flow system is adopted which uses a first solution (sample solution) containing the first compound representing an object to be measured and a second solution (low molecular compound solution) containing the second compound representing a ligand.

The NMR measurement apparatus further comprises a mixing filter for mixing the first solution and the second solution and a separation filter for separating them, a first flow channel through which the first solution drained out of the separation filter is injected to the mixing filter, a second flow channel through which the second solution drained out of the separation filter is injected to the mixing filter, and a third flow channel through which the mixture solution drained out of the mixing filter is injected to the separation filter by way of the reservoir.

The construction of the NMR measurement apparatus, an operating method and an NMR measuring method in the invention disclosed in the present application will be described.

(Construction of NMR Measurement Apparatus)

The NMR measurement apparatus has a magnet for generating a static magnetic field, an antenna for emitting or irradiating an electromagnetic wave to a sample and detecting an FID signal originating from the sample, a transmission unit for generating the irradiation electromagnetic wave, a reception unit for processing the detected FID signal, and a reservoir for fixing the sample at a location suitable for NMR measurement. Provided for the reservoir are a pipe for injecting the sample to the reservoir and a pipe for draining the sample out of the reservoir.

Connected to the pipe for injecting the sample (first sample conveyance pipe) is a filter (mixing filter) for mixing a low molecular compound solution and a high molecular compound solution (sample solution). The mixing filter has three ports of a low molecular compound solution injection port, a sample solution injection port and a mixture solution drainage port for a mixture solution of the low molecular compound solution and the sample solution, and the first sample conveyance pipe is connected to a drainage port of the mixing filter. The sample solution injection port is attached with a flow path switchover or transfer valve (first valve).

A pipe for draining the mixture solution from the reservoir (second sample conveyance pipe) is connected with a filter (separation filter) for separating the low molecular compound solution and the sample solution. The separation filter has three ports of a sample solution drainage port, a low molecular compound solution drainage port and a mixture solution injection port and the second sample conveyance pipe is connected to the mixture solution injection port. The sample solution drainage port is attached with a flow path switchover or transfer valve (second valve).

Then, the first and second valves are connected by means of a pipe (third sample conveyance pipe), so that a flow path or channel can be formed through which the sample solution can circulate.

Further, the low molecular compound solution drainage port of separation filter is connected to an injection port of a low molecular compound solution controller by means of a pipe (fourth sample conveyance pipe). A drainage port of the low molecular compound solution controller is connected to the low molecular compound solution injection port of mixing filter by means of a pipe (eighth sample conveyance pipe). With the above arrangement, a flow channel can be formed through which the low molecular compound solution circulates by way of the low molecular compound solution controller, mixing filter and separation filter to return to the low molecular compound solution controller.

The low molecular compound solution controller is comprised of a valve for drainage, a low molecular compound solution injecting unit, a valve for water injection and a circulating pump. The drainage valve and the low molecular compound injecting unit are connected by means of a fifth sample conveyance pipe. The low molecular compound injecting unit and the water injection valve are connected by means of a sixth sample conveyance pipe. The valve for injecting water and the circulating pump are connected by means of a seventh conveyance pipe.

With the above construction and flow channels, two circulation flow channels can be established including a looped flow channel through which the mixture solution of high molecular compound and low molecular compound passes and a flow channel through which a circulative flow of the low molecular compound solution can be materialized. With this construction, injection of the low molecular compound solution, injection of the high molecular compound solution, circulation of the low molecular compound solution and uniformity control of the mixture solution independent of adjustment of the low molecular compound solution can be achieved.

Further, in the first sample conveyance pipe or second sample conveyance pipe representing the passage for the mixture solution, a circular dichronism spectrometer or a Raman spectrometer is arranged. An absorbance meter (concentration meter) and a hydrogen ion concentration meter (pH meter) which are suitable for concentration measurement are arranged in the first and second sample conveyance pipes, respectively. Then, in any one of the fourth, fifth, sixth, seventh and eighth sample conveyance pipes through which only the low molecular compound solution passes, the concentration meter or the hydrogen ion concentration meter (pH meter) is arranged. Each of the thus arranged circular dichronism spectrometer, Raman spectrometer, absorbance meter (concentration meter) and hydrogen ion concentration meter (pH meter) has the function to display or record a set of each measurement-executed time and data or to transfer data. Individual timers attached to the individual measuring instruments or built therein can be adjustable to indicate identical times.

(Method of Measuring Low Molecular Compound Concentration)

Next, measurement of low molecular compound concentration in the above-described construction will be described.

The low molecular compound concentration is measured by using the concentration meter arranged in at least one of the fourth, fifth, sixth, seventh and eighth sample conveyance pipes. A concentration measuring method utilizing the absorbance meter (concentration meter) is a widely known one. In the installed concentration meter, a set of measurement-executed time and concentration data is displayed or recorded. The set of measurement-executed time and concentration data is recorded in a computer with recording medium or on a paper. The concentration measurement and the record of a set of measurement-executed time and concentration data are carried out consecutively during a time interval ranging from start designation to end designation by a measurer.

(Operation of Mixture Solution)

Next, operation of the solution state of high molecular compound and low molecular compound in the aforementioned construction will be described.

An absorbance value of a mixture solution is measured using the absorbance meter (concentration meter) arranged in the first or second sample conveyance pipe. A wavelength to be measured is selected in accordance with characteristics of high molecular compound and low molecular compound to be injected. In the case of an absorbance meter with spectroscopic function, the measurement wavelength selection is fulfilled in terms of selection of an observation band. The absorbance of the solution changes as a solvent changes and therefore, when a high molecular compound mixes in a solution in which only a low molecular compound exists, the absorbance changes in accordance with the quantity (concentration) of the high molecular compound. By taking advantage of this change, the position of the injected high molecular compound is decided and the uniformity of concentration of the mixture solution is evaluated.

If circulation of the mixture solution is not executed, the first and second valves are operated to set up such a flow channel that the mixture solution does not pass through the third sample conveyance pipe. At that time, a high molecular compound injected from the injection syringe attached to the first valve migrates to the drainage syringe attached to the second valve by way of the mixing filter, first sample conveyance pipe, reservoir, second sample conveyance pipe, separation filter and second valve.

In order to conduct an NMR measurement, a high molecular compound needs to be held in the reservoir during the measurement. To monitor migration of the high molecular compound from the injection syringe to the reservoir, the absorbance meter provided for the first sample conveyance pipe is utilized. Also, for monitoring migration of the high molecular compound from the reservoir to the drainage syringe, the absorbance meter provided for the second sample conveyance pipe is utilized. During the period ranging from monitor start designation to monitor end designation by the measurer, the measurement of absorbance and recording a set of measurement-executed time and absorbance data are carried out sequentially.

After the high molecular compound has been injected, the absorbance of the absorbance meter provided for the first sample conveyance pipe changes. Thereafter, at the time that the absorbance of the absorbance meter provided for the second sample conveyance pipe changes, the circulation of solution is stopped and an NMR measurement is started. At that time, the high molecular compound is held in the reservoir so as to be placed in condition suitable for an NMR measurement of the solution containing the high molecular compound. After completion of the NMR measurement, the solution starts circulating. Subsequently, when the values of the absorbance meters provided for the first and second sample conveyance pipes return to a value similar to that of the low molecular compound solution, the high molecular compound is drained out of the reservoir and is in a condition that it has migrated from the second sample conveyance pipe to the separation filter. In this manner, when the circulation of the mixture solution does not proceed, the high molecular compound can be migrated/held by only turning on/off the circulation operation with the help of the circulating pump. Thereafter, the high molecular compound is collected using the syringe for drainage.

On the other hand, in order to conduct the circulation of a mixture solution, the first and second valves are operated to set up a flow channel for enabling the mixture solution to pass through the third sample conveyance pipe. In this case, two procedures of injection and drainage of a high molecular compound which resort to the valve operation are necessary. In the injection procedure, the high molecular compound is first injected from the injection syringe attached to the first valve. Then, the first valve is switched over so that the flow channel is switched from the injection syringe to the third sample conveyance pipe. A solution containing the high molecular compound reaches the third sample conveyance pipe and then the first valve by way of the mixing filter, first sample conveyance pipe, reservoir, second sample conveyance pipe, separation filter and second valve. Since the flow channel associated with the high molecular compound is closed, the high molecular compound circulates through the route as above. With a view to promoting the efficiency of circulation, a second pump for circulation may be provided for the third sample conveyance pipe.

Changes in solution state during the circulation are consecutively monitored with the absorbance meters provided for the first and second sample conveyance pipes. Subsequently, when fluctuation of values with time of the absorbance meter provided for the first sample conveyance pipe substantially equals that of the absorbance meter provided for the second sample conveyance pipe, the concentration of the high molecular compound in the mixture solution is so determined as to be uniformed. In this state, the high molecular compound fills the reservoir at a uniform concentration and therefore the circulation is stopped to start an NMR measurement.

In the drainage procedure after completion of the NMR measurement, the first and second valves are first operated to close the flow path to the third sample conveyance pipe. Thereafter, with circulation of the low molecular compound solution started, the high molecular compounds gradually gather to a connection part between the separation filter and the second valve. Then, when values of the absorbance meters provided for the first and second sample conveyance pipes approach a value the low molecular compound alone assumes, the flow path of the second valve is transferred to the drainage syringe and the solution containing the high molecular compound is collected.

The first and second valves are again switched to the third sample conveyance pipe to set up a closed loop for the mixture solution, permitting the mixture solution to circulate. Then, when values of the absorbance meters provided for the first and second sample conveyance pipes again approach a value the mixture solution assumes, the first and second valves are operated to close the flow path to the third sample conveyance pipe and the high molecular compound can be collected with the help of the drainage syringe under the circulation of the low molecular compound solution.

(Titration Measuring Method)

A description will be given of a measuring method when in sample solution adjustment based on the circulation-flow scheme, the concentration of a low molecular compound is changed at a constant concentration of a high molecular compound.

(Water Injection)

Firstly, the water injection valve and drainage valve are opened and the first and second valves are both switched to the flow path to the third sample conveyance pipe. Next, the circulating pump is driven and pure water is injected from the water injection valve. The pure water flows through the eighth sample conveyance pipe, fills the mixing filter and reaches both the drainage port and the sample solution injection port. The pure water reaching the drainage port of mixing filter passes through the first sample conveyance pipe, reservoir and second sample conveyance pipe, arriving at the separation filter. Similarly, after reaching the sample solution injection port of mixing filter, the pure water passes through the first valve, third sample conveyance pipe and second valve, coming to the separation filter. After reaching the separation filter, the pure water flows through the fourth sample conveyance pipe and is then drained out of the drainage valve.

(Exchange with Buffer Liquid)

The circulating pump is once stopped and the connection of the entrance of the water injection valve is exchanged for a reservoir of a buffer liquid. Thereafter, the circulating pump is driven to forward the buffer liquid to the whole of circulation channel. After completion of forwarding, the water injection valve is closed.

(Injecting and Uniformizing High Molecular Compound)

Assumptively, circulation is carried out by means of the circulating pump and the flow path associated with the first valve is transferred to the injection syringe. Then, a high molecular compound is injected from the injection syringe attached to the first valve. Thereafter, the first valve is transferred so that the flow channel is switched from the injection syringe to the third sample conveyance pipe. A solution containing the high molecular compound flows through the mixing filter, first sample conveyance pipe, reservoir, second sample conveyance pipe, separation filter and second valve to reach the third sample conveyance pipe and first valve. Since the flow channel associated with the high molecular compound is closed, the high molecular compound circulates through the aforementioned route. During the circulation, changes in solution state are consecutively monitored with the absorbance meters provided for the first and second sample conveyance pipes, respectively. Subsequently, when fluctuation of values with time of the absorbance meter provided for the first sample conveyance pipe substantially equals that of the absorbance meter provided for the second sample conveyance pipe, the concentration of the high molecular compound in the mixture solution is so determined as to be uniformized.

(Titration Measurement)

A description will hereinafter be given of a process in which a low molecular compound solution is injected so as to increase the low molecular compound concentration in the circulation channel. A titration measurement can be carried out in which a solution not containing a specified low molecular compound is used to conduct the same procedure so that the concentration of the specified low molecular compound alone may be decreased. Firstly, the concentration meter provided for the fourth, fifth, sixth, seventh or eighth sample conveyance pipe is used to start a low molecular compound concentration measurement. Next, the circulating pump is driven to start solution circulation. Then, a syringe pump for low molecular compound solution injection is used to inject the low molecular compound solution to the circulation channel. When the value of the concentration meter for the low molecular compound has converged to a constant value or a constant range of fluctuations, the uniformity of the low molecular compound concentration inside the circulation channel is determined. When the low molecular compound concentration reaches a target concentration, the circulation is stopped and a measurement is conducted.

If the low molecular compound concentration is lower than the target concentration, the process for injecting the low molecular compound solution is carried out to increase the concentration. If the low molecular compound concentration is higher than the target concentration, the injection process is carried out with a solution not containing the low molecular compound to decrease the concentration. In respect of all low molecular compound concentration conditions which have been set by the measurer, the process for increasing or decreasing the low molecular compound concentration and the measurement are conducted.

(Measurement)

The measurement referred to herein includes, in addition to the NMR measurement, measurements with the help of other measuring instruments provided for the first and second sample conveyance pipes (absorbance meter, circular dichroism spectrometer, Raman spectrometer and electrical conductivity meter).

The meritorious effect attainable by a typical one of inventions disclosed in the present application will be described in brief as below.

More particularly, according to an embodiment of the present invention, the controllability of the NMR measurement apparatus can be improved by the circulation flow scheme in which the quantity of a second compound relative to a first compound representing a measuring object is changed in accordance with the concentration of a second compound solution.

Other objects, features and advantages of the invention will become apparent from the following description of the embodiments of the invention taken in conjunction with the accompanying drawings.

DETAILED DESCRIPTION OF THE EMBODIMENTS

Figure 1:
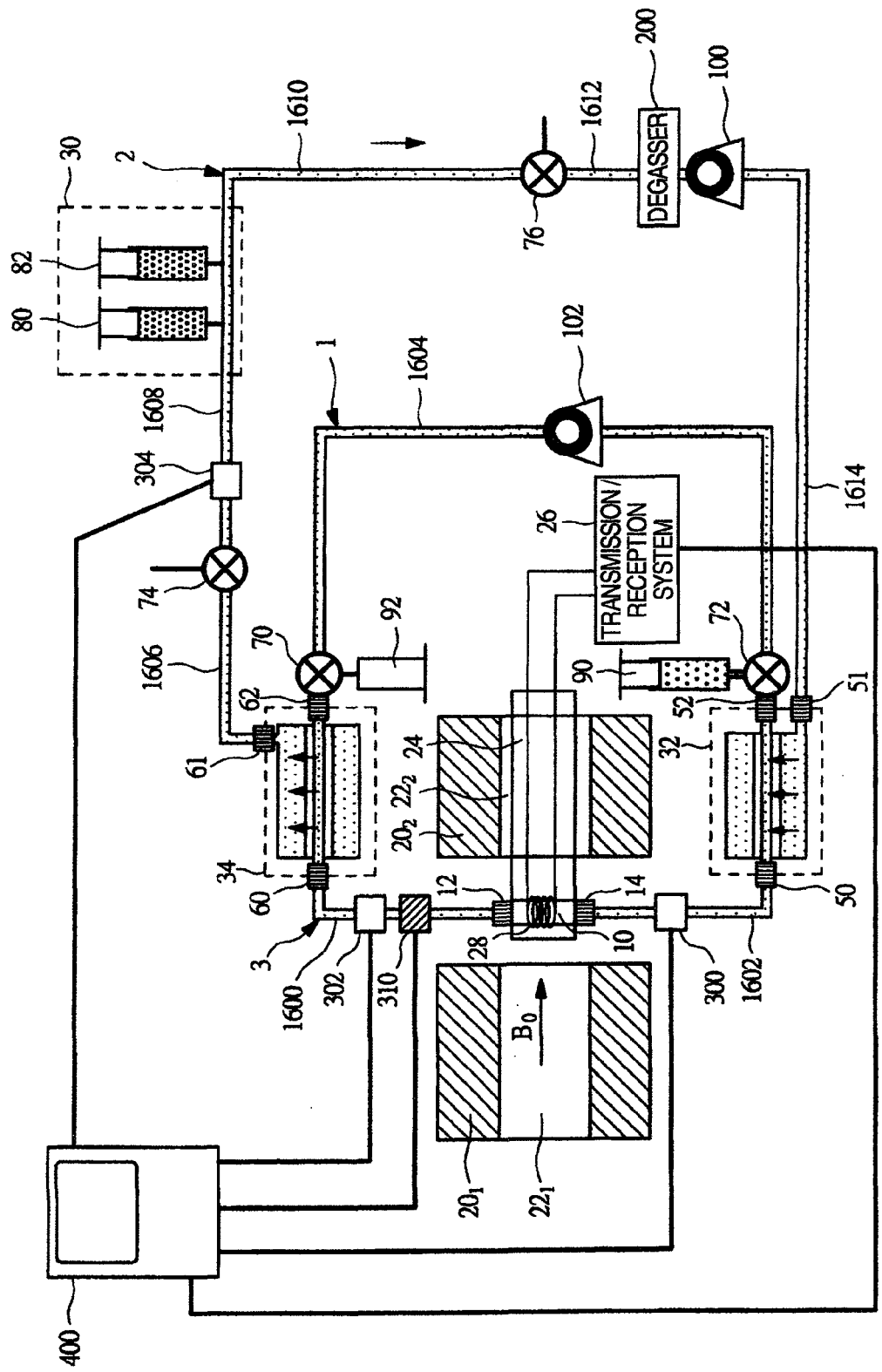
FIG. 1 is a diagram schematically illustrative of the construction of an NMR measurement apparatus according to an embodiment of the present invention.

Embodiments of this invention will now be described in detail with reference to the accompanying drawings. In all Figures illustrative of the embodiments, members identically functioning are designated by identical reference numerals and a reiterative description will not sometimes be given of them. In addition, in the Figures illustrative of the following embodiments, hatching will sometimes be applied for better understanding of the construction.

Embodiment 1

An NMR measurement apparatus according to the present invention is a one which performs NMR measurement of a mixture solution containing a high molecular compound such as protein and a low molecular compound having a molecular weight smaller than the high molecular compound and in the apparatus, for example, a change in NMR spectrum can be measured while freely controlling the concentration ratio between the low molecular compound and the high molecular compound under a constant amount of the high molecular compounds.

Preferred embodiments of the apparatus construction which can conduct an NMR measurement concurrently with other kinds of measurements and besides can improve concentration control in the course of titration measurement utilizing sample solution adjustment based on the circulation flow scheme of the present invention and a method therefor will be described hereunder with reference to the accompanying drawings.

(Construction of NMR Measurement Apparatus)

Firstly, the arrangement of flow channels through which a sample solution flows will be described. As shown in FIG. 1, a nuclear magnetic resonance probe 24 is placed in a space (bore) 22 formed interiorly of a split type magnet 20 adapted to apply a magnetic field to a sample. In the nuclear magnetic resonance probe 24, a reservoir 10 adapted to hold the sample, having a injection port 14 and a drainage port 12 for the sample, is disposed. A first sample conveyance pipe 1602 is connected to the injection port 14 of reservoir 10. Then, the first sample conveyance pipe 1602 is connected with a mixing filter 32 for mixing a low molecular compound solution and a sample solution (high molecular compound solution). Provided for the mixing filter 32 are a low molecular compound solution injection port 51, a sample solution injection port 52 and a mixture solution drainage port 50. The mixture solution drainage port 50 is connected with the first sample conveyance pipe 1602. A second sample conveyance pipe 1600 is connected to the drainage port 12 of reservoir 10.

The second sample conveyance pipe 1600 is connected with a separation filter 34 for separating the low molecular compound solution and the sample solution. Provided for the separation filter 34 are a sample solution drainage port 62, a low molecular compound solution drainage port 61 and a mixture solution injection port 60. The mixture solution injection port 60 is connected with the second sample conveyance pipe 1600. A first valve 72 is connected to the sample solution injection port 52 of mixing filter 32. Similarly, a second valve 70 is connected to the sample solution drainage port 62 of separation filter 34.

One entrance port of first valve 72 and one entrance port of second valve 70 are interconnected by way of a third sample conveyance pipe 1604. The low molecular compound drainage port 61 of separation filter 34 is connected with a fourth sample conveyance pipe 1606. Connected to the fourth sample conveyance pipe 1606 is a drainage valve 74. A fifth sample conveyance pipe 1608 is connected to the drainage valve 74. The fifth sample conveyance pipe 1608 is connected with a low molecular compound solution injecting unit 30. The low molecular compound solution injecting unit 30 is connected with a sixth sample conveyance pipe 1610. A valve 76 for water injection is connected to the sixth sample conveyance pipe 1610. The water injection valve 76 is connected with a seventh sample conveyance pipe 1612. The seventh sample conveyance pipe 1612 is connected with a circulating pump 100. The circulating pump 100 is connected to the low molecular compound solution injection port 51 of mixing filter 32 by way of an eighth sample conveyance pipe 1614.

With the construction and flow channels as above, two circulation flow channels can be established including a looped flow channel through which a mixture solution of high molecular compound and low molecular compound passes and a flow channel that realizes a circulative flow of a low molecular compound solution.

The construction of the NMR measurement apparatus according to the present embodiment will be outlined herein. The NMR measurement apparatus comprises the reservoir 10 for holding a mixture solution containing a high molecular compound and a low molecular compound of lower molecular weight than that of the high molecular compound, the magnet 20 for applying a magnetic field to the mixture solution held in the reservoir 10 and the nuclear magnetic resonance probe 24 attached to the reservoir 10. The reservoir 10 is made of, for example, quartz glass. The magnet 20 is formed of, for example, a super-conducting magnet and can generate a magnetic field corresponding to, for example, 300 MHz to 1 GHz. The NMR probe 24 includes, for example, a coil 28 wound about the reservoir 10 and from the coil, an electromagnetic wave pulse can be emitted or irradiated to the mixture solution representing a measuring target to detect an NMR signal.

The NMR measurement apparatus according to the present embodiment further comprises the mixing filter 32 for mixing a sample solution containing the high molecular compound and a low molecular compound solution containing the low molecular compound and for draining a resulting mixture solution and the separation filter 34 for separating the mixture solution injected thereto to the sample solution and the low molecular compound solution. The mixing filter 32 and separation filter 34 are not particularly limitative as far as they can participate in separation between the high molecular compound such as protein and other components but preferably, each of them is formed of a hollow member of threaded mesh film having small perforations of such a diameter as blocking passage of the high molecular compound but permitting passage of other components including the low molecular compound. In other words, because the size of the small perforation of hollow threaded mesh film can be selected for use in compliance with the molecular weight of the high molecular compound in the mixture solution, an operation of ultrafiltration of components other than the high molecular compound (for example, the low molecular compound) can preferably be carried out.

The NMR measurement apparatus according to the present embodiment further comprises pipes for constituting, respectively, a channel 1 adapted to inject the sample solution drained out of the separation filter 34 to the mixing filter 32, a channel 2 adapted to inject the low molecular compound solution drained out of the separation filter 34 to the mixing filter 32 and a channel 3 adapted to inject the mixture solution drained out of the mixing filter 32 to the separation filter 34 by way of the reservoir 10. In the NMR measurement apparatus shown in FIG. 1, the third sample conveyance pipe 1604 constitutes the channel 1. The fourth, fifth, sixth, seventh and eighth sample conveyance pipes 1606, 1608, 1610, 1612 and 1614 constitute the channel 2. The first and second sample conveyance pipes 1602 and 1600 constitute the channel 3. The material of the pipe of each of the channels 1 to 3 should be selected in accordance with, for example, the nature of an NMR measuring target and in measurement of such a high molecular compound related to a living body as protein, for example, polyethylene ethylene-ketone (PEEK) can be used. The inner diameter of the pipe can fall within a range of, for example, 0.5 to 0.065 mm.

Moreover, the NMR measurement apparatus according to the present embodiment further comprises the injecting unit 30 provided for the channel 2 and adapted to inject a low molecular compound mixture solution in which the concentration of the low molecular compound is adjusted to a predetermined value and the circulating pump 100 also provided for the channel 2 and adapted to circulate the low molecular compound solution through the channels 2 and 3. In the injecting unit 30, syringe pumps of pressurizing type, for example, can be controlled electronically and the unit 30 can preferably work pressurized forwarding of liquid while controlling a low molecular compound solution injection syringe 80 fed with a low molecular compound content solution to inject the low molecular compound solution to the channel 2. Similarly, the injecting unit 30 can inject a buffer liquid to the channel 2 by working pressurized forwarding of liquid while controlling a buffer liquid injection syringe 82. Preferably, a circulating pump used in high-rate liquid chromatography, for example, can be used as the circulating pump 100. More preferably, the circulating pump is of the type in which a plunger can be driven using an electronically controllable stepping motor to forward a liquid to the reservoir 10 and channel 2 under a constant pressure.

With the NMR measurement apparatus in the present embodiment as constructed above, the concentration controllability can be improved through the circulation flow scheme in which the amount of the low molecular compound (second compound) relative to the high molecular compound (first compound) representing a measuring target can be changed by the concentration of the low molecular compound solution.

Figure 2:
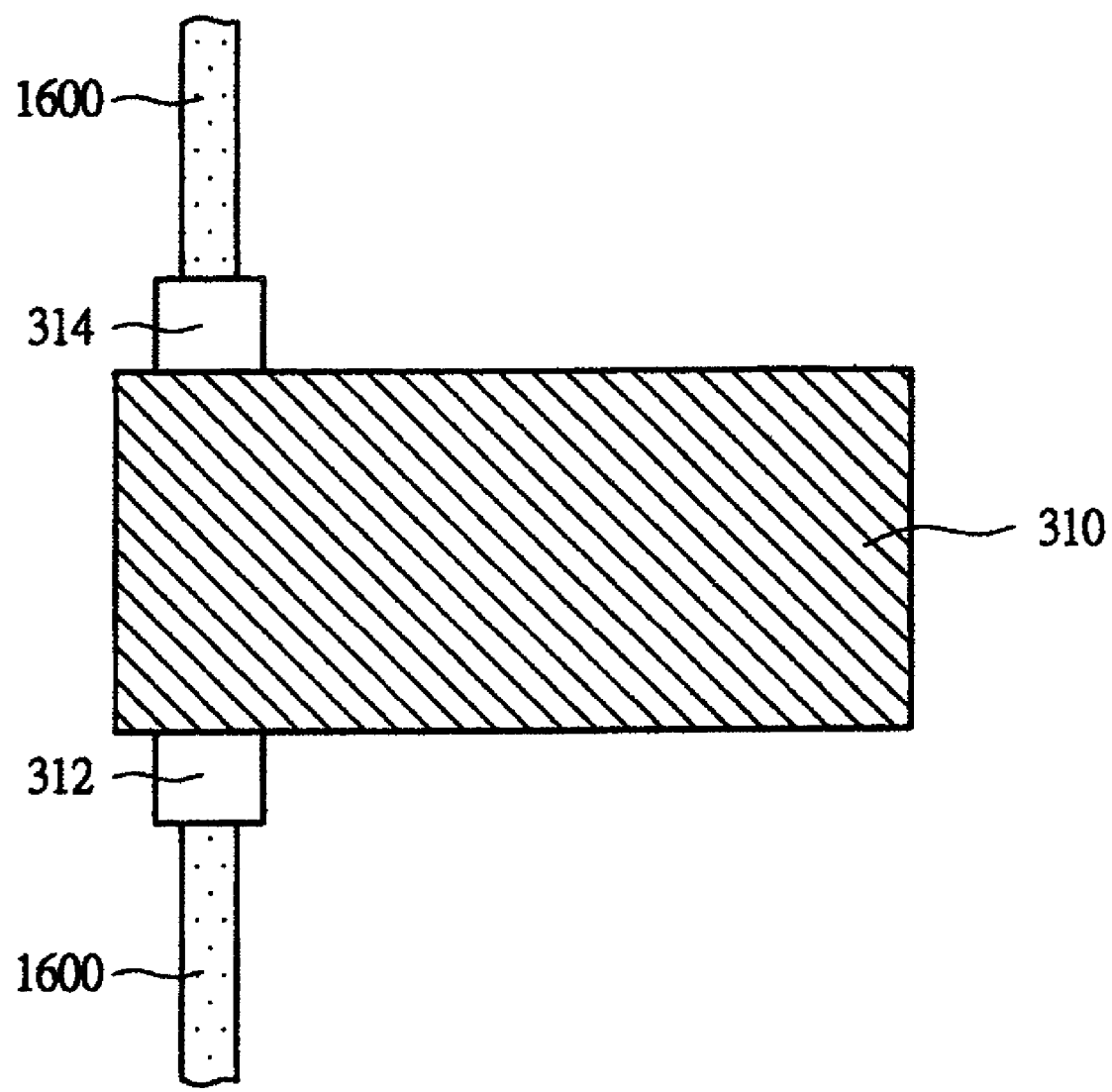
FIG. 2 is a diagram schematically illustrative of the connection of a measuring instrument provided for the FIG. 1 NMR measurement apparatus.

Next, the arrangement of measuring instruments will be described. As shown in FIG. 1, a measuring instrument 310 as represented by, for example, a circular dichroism spectrometer (CD meter) is provided for the first sample conveyance pipe 1602 or the second sample conveyance pipe 1600. An example of mounting the meter to the second sample conveyance pipe 1600 is illustrated in FIG. 2. The second sample conveyance pipe 1600 is halved and the measuring instrument 310 in the form of the CD meter is interposed between the halves. The two parts of second sample conveyance pipe 1600 are connected to solution entrance 312 and solution exit 314 of the measuring instrument, respectively. For connection, a method is preferably used which utilizes fitting well known to workers handling such a solution as HPLC. The measuring instrument 310 in the form of CD meter has the function to record or display a set of measurement-executed time and measured value or to transfer data.

First and second concentration meters 300 and 302 are provided for the first sample conveyance pipe 1602 and the second sample conveyance pipe 1600, respectively. Setting the first and second concentration meters 300 and 302 is carried out through a method similar to the setting example of the measuring instrument 310 in the form of CD meter as shown in FIG. 2. The first and second concentration meters 300 and 302 are for measuring the absorbance of the solution. By taking advantage of such a principle that the proportional relation stands between the solution concentration and the absorbance, a concentration can be calculated from a measured absorbance. Each of the first and second concentration meters 300 and 302 has the function to measure the absorbance, to record or display a set of measurement-executed time and measured value or to transfer data. Or, the calculated concentration may additionally be subjected to recording, display or data transfer.

Between the low molecular compound solution injection port 51 of mixing filter 32 and the low molecular compound drainage port 61 of separation filter 34 which are connected to each other by way of the fourth, fifth, sixth, seventh and eighth sample conveyance pipes 1606, 1608, 1610, 1612 and 1614, a third concentration meter 304 is arranged. Setting the third concentration meter is carried out through a method similar to the setting example of the measuring instrument 310 as shown in FIG. 2. The third concentration meter 304 also has the function to measure the absorbance, to record or display a set of measurement-executed time and measured value or to transfer data. Or, the calculated concentration may additionally be subjected to recording, display or data transfer.

Each of the set measuring instrument 310 and the first to third concentration meters 300, 302 and 304 can display a set of measurement-executed time and measured value or can transfer data and hence, the observer can compare these pieces of data on the real time base.

The transmission/reception system 26 for recording NMR signals, the first, second and third concentration meters 300, 302 and 304 and the measuring instrument 310 in the form of CD meter are connected to a computer 400 adapted to collect and display data from these meters as shown in FIG. 1. By using the data transfer function of the individual meters in this manner, a set of measurement-executed time and measured value by each meter can be recorded and the individual measured values can be compared with one another on the time base.

Further, as shown in FIG. 1, a degasser 200 may be provided on the side of seventh sample conveyance pipe 1612 of the circulating pump 100. Also, in order to promote the circulation efficiency, a second circulating pump 102 may be provided for the third sample conveyance pipe 1604. In respect of the measuring instrument 310, a Raman spectrometer, a pH meter or an electrical conductivity meter substituting for the CD meter may be arranged to perform a measurement concurrently with the NMR measurement.

(Titration Measurement Procedure)

In the titration measurement using the NMR measurement apparatus according to the present embodiment, the concentration of a low molecular compound can be changed freely while keeping the concentration of a high molecular compound constant. The procedure of titration measurement for changing the concentration ratio between the high molecular compound and the low molecular compound will be described.

As the high molecular compound, protein of widely usable kinds can be used and as the low molecular compound, medicine candidate compounds (ligand) can be used. A buffer liquid is so selected as to meet the nature of each kind of protein. As a preferable example, a combination of cattle blood serum protein representing the high molecular compound, L-triptophan representing the low molecular compound and phosphoric acid buffer representing the buffer liquid will be adopted.

Figure 3:
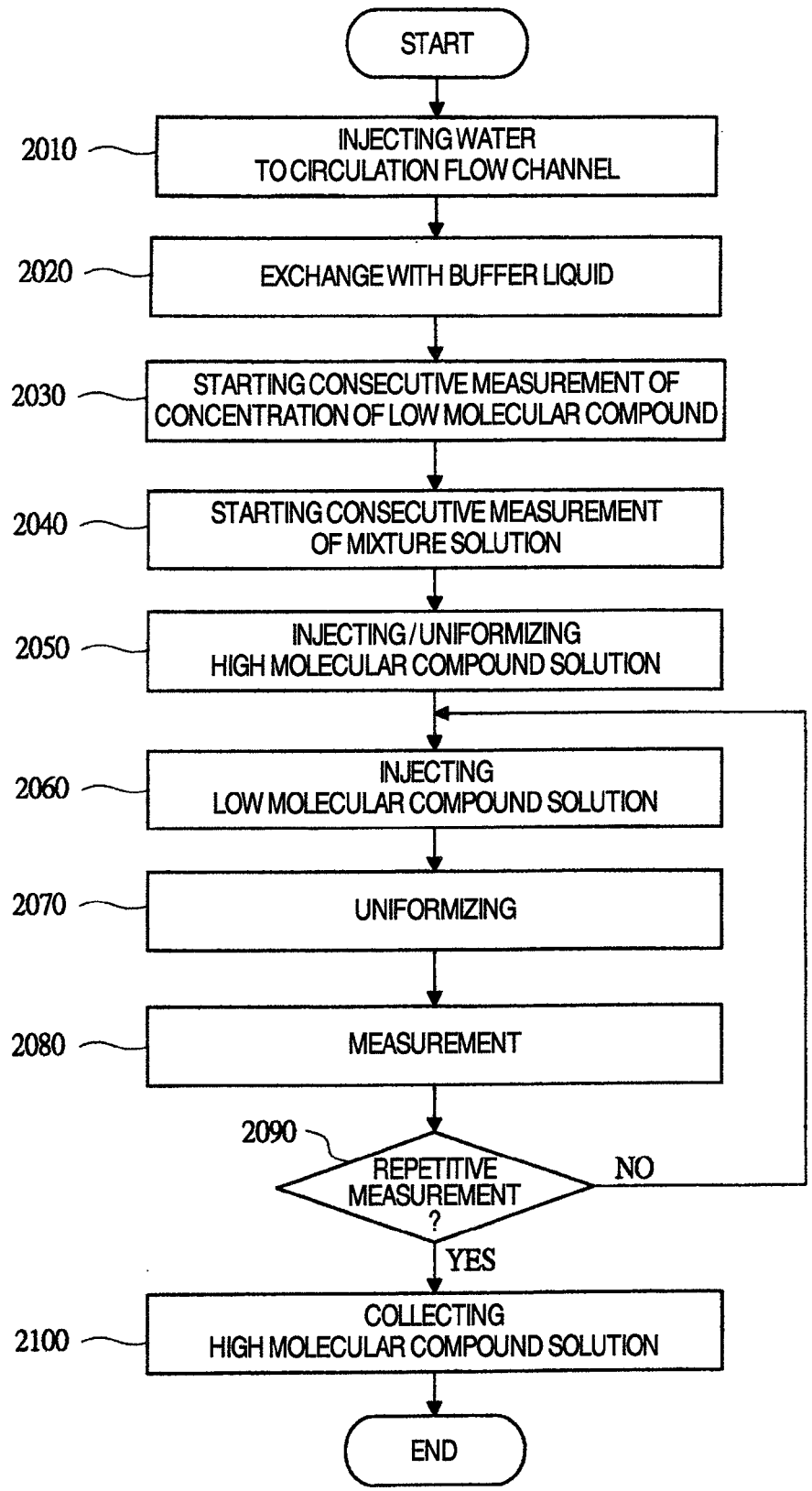
FIG. 3 is a flowchart of an embodiment of measurement in the NMR measurement apparatus according to the FIG. 1 embodiment of the invention.

The procedures in the whole of titration measurement will be outlined with reference to a flowchart of FIG. 3. Firstly, step 2010 of injecting water to the circulation channel and step 2020 of exchange with the buffer liquid are conducted to fill up the whole circulation channel with a solution. Next, step 2030 of starting consecutive measurement of the concentration of the low molecular compound and step 2040 of starting consecutive measurement of the mixture solution are conducted. Then, step 2050 of injecting the high molecular compound solution and uniformizing the high molecular compound solution is conducted to make uniform the concentration in the circulation channel inclusive of the reservoir 10. Then, step 2060 of injecting the low molecular compound solution, step 2070 of uniformizing the low molecular compound concentration uniform and step 2080 of measurement are carried out repetitively while making adjustments of concentration. After completion of the measurement, the high molecular compound is collected and the circulation channel is cleaned with pure water.

In the procedures mentioned as above, as the repetition of injecting the low molecular compound solution and making uniform the concentration thereof proceeds, a surplus volume containing the low molecular compound solution is drained out of the drainage valve 74 whereas the low molecular compound concentration in the circulation channel increases. On the other hand, the high molecular compound is confined within the circulation channel inclusive of the reservoir 10 by means of the mixing filter 32 and separation filter 34 and consequently, cannot be drained whenever the low molecular compound solution is injected. Accordingly, the concentration of the high molecular compound remains constant. If a solution not containing the target low molecular compound is injected in place of the low molecular compound solution, the low molecular compound concentration in the circulation channel decreases, failing to keep the high molecular compound concentration constant.

(Step 2010 of Injecting Water to Circulation Channel)

Firstly, the water injection valve 76 and the drainage valve 74 are opened and both the first and second valves 72 and 70 are switched to the flow path to the third sample conveyance pipe 1604. Next, the circulating pump 100 is driven to inject pure water from the water injection valve 76. The pure water flows through the eighth sample conveyance pipe 1614 to fill the mixing filter 32, reaching both the mixture solution drainage port 50 and the sample solution injection port 52. Thereafter, the pure water reaching the mixture solution drainage port 50 of mixing filter 32 flows through the first sample conveyance pipe 1602, reservoir 10 and second sample conveyance pipe 1600, arriving at the separation filter 34. Similarly, the pure water reaching the sample solution injection port 52 of mixing filter 32 flows through the first valve 72, third sample conveyance pipe 1604 and second valve 70, coming to the separation filter 34. The pure water arriving at the separation filter 34 flows through the fourth sample conveyance pipe 1606 and reaches the drainage valve 74.

(Step 2020 of Exchange with Buffer Liquid)

The circulating pump 100 is once stopped and the entrance of water injecting valve 76 is switched to a reservoir of the buffer liquid. Thereafter, the circulating pump 100 is driven to forward the buffer liquid to the whole of circulation channel. After completion of forwarding, the water injection valve 76 is closed.

(Step 2030 of Starting Consecutive Measurement of Low Molecular Compound Concentration)

With the third concentration meter 304 used, consecutive measurement of the concentration of the low molecular compound is started. A wavelength to be measured is so selected as to meet characteristics of the high molecular compound and low molecular compound to be injected. When an absorbance meter with spectroscopic function is used, the measurement wavelength selection is fulfilled in terms of selection of an observation band. Preferably, the measurement is conducted at intervals of 1 second to 10 minutes.

(Step 2040 of Starting Consecutive Measurement of Mixture Solution)

Consecutive measurement of the absorbance of a mixture solution is started using the first and second concentration meters 300 and 302. A wavelength to be measured is so selected as to meet characteristics of a high molecular compound and a low molecular compound which are to be injected. In the case of an absorbance meter with spectroscopic function, the measurement wavelength selection is fulfilled in terms of selection of an observation band. Preferably, the measurement is conducted at intervals of 1 second to 10 minutes. After the start of measurement, such a condition lasts for a while that absorbance values observed by the first to third concentration meters are substantially equal to one another or fluctuate substantially equally.

In the event that remarkably different values are observed in this phase, contamination and damage of the circulation channel constituent parts are conceivable and so stoppage of the measurement and making an inspection are recommended.

(Step 2050 of Injecting/Uniformizing High Molecular Compound Solution)

Circulation by the circulating pump 100 proceeds and the flow path of the first valve 72 is switched over to the sample solution injection syringe 90. In the injecting process, a high molecular compound is first injected from the sample solution injection syringe 90 attached to the first valve 72. Then, the first valve 72 is transferred so as to switch the flow path from the sample solution injection syringe 90 to the third sample conveyance pipe 1604. The solution containing the high molecular compound flows through the mixing filter 32, first sample conveyance pipe 1602, reservoir 10, second sample conveyance pipe 1600, separation filter 34 and second valve 70, coming to the third sample conveyance pipe 1604 and first valve 72. Since the flow path for the high molecular compound is closed, the high molecular compound circulates through the route as above. Changes in solution state during the circulation are sequentially monitored by means of the first and second concentration meters. Next, when values of the first and second concentration meters become equal to each other and fluctuate substantially equally, the concentration of the high molecular compound in the mixture solution is determined as being uniform.

As shown in FIG. 1, in order to promote the efficiency of circulation, the second pump 102 for circulation may be provided for the third sample conveyance pipe 1604.

(Titration Measurement)

A process of injecting the low molecular compound to increase the concentration of the low molecular compound in the circulation channel will be described herein. By executing the same procedure by using a solution not containing a specified low molecular compound, a titration measurement in the course of decreasing the concentration of only the specified low molecular compound can be carried out.

(Steps 2060 and 2070 of Injecting/Uniformizing Low Molecular Compound Solution)

Firstly, the circulating pump 100 is driven to start solution circulation. Then, the low molecular compound solution is injected to the circulation channel by using the low molecular compound solution injection syringe 80 of low molecular compound solution injecting unit 30. When the value of the third concentration meter 304 for low molecular compound converges to a constant value or falls within a constant range of fluctuations, the low molecular compound concentration in the circulation channel is determined as being uniform.

If the low molecular compound concentration is lower than a target concentration, the process for injecting the low molecular compound solution is conducted to increase the concentration. If the low molecular compound concentration is higher than the target concentration, a solution not containing the low molecular compound is injected from the syringe 82 for buffer liquid injection, thus making an adjustment through concentration unification based on the circulation.

(Step 2080 of Measurement, Step 2090 of Repetitive Measurement)

When the concentration of the low molecular compound reaches the target concentration, the circulation is stopped and an NMR measurement starts. For all low molecular compound concentration conditions set by the measurer, the process of increasing or decreasing the low molecular compound concentration and the measurement are carried out.

The measurement referred to herein includes, in addition to the NMR measurement, measurements by means of other measuring instruments provided for the first and second sample conveyance pipes 1602 and 1600 (absorbance meter, CD meter, Raman spectrometer and electrical conductivity meter).

In the present invention, under the condition that the solution environment such as low molecular compound concentration or hydrogen ion concentration changes, the measurement based on the NMR probe and measurements by other measuring instruments can be conducted. In the NMR measurement, changes in molecular mobility or migration and molecular structure can be observed in response to a nuclear spin of a sample molecule. On the other hand, in the absorbance meter and CD meter, a change in the secondary structure of a sample molecule can be observed from an absorption/reflection coefficient of a polarized ray of light passing through the sample solution. Also, in the Raman spectroscopy, changes in structure can be observed from molecular vibration of a sample molecule.

As described above, in this invention, various observations probed through different physical processes can be achieved in respect of a sample molecule in a solution. The data is obtained on the condition that the solution is the same and the measurement-executed time is the same and therefore, as compared to pieces of data measured solely for individually prepared samples, a set of more complementary experimental data can be offered and the relation between the structure change and the chemical function can be clarified.

(Step 2100 of Draining High Molecular Compound)

In the drainage process after completion of the NMR measurement, on the other hand, the flow path to the third sample conveyance pipe 1604 is closed in the first and second valves 72 and 70. Subsequently, when circulation of the low molecular compound solution is started, the high molecular compounds gradually gather to a portion where the second valve 70 connects to the separation filter 34. Then, when values of the absorbance meters provided for the first and second sample conveyance pipes 1602 and 1600 approach a value of the low molecular compound alone, the flow path of second valve 70 is transferred to the sample solution collecting syringe 92 and the solution containing the high molecular compound is collected.

The first and second valves 72 and 70 are again transferred to the third sample conveyance pipe 1604 to set up a closed loop for the mixture solution, thus causing the mixture solution to circulate. Then, when values of the absorbance meters provided for the first and second sample conveyance pipes 1602 and 1600 again approach the value of the mixture solution, the first and second valves 72 and 70 are so operated as to close the flow path to the third sample conveyance pipe 1604 and through the circulation of the low molecular compound solution, the high molecular compound is collected by means of the sample solution collection syringe 92. By repeating the above procedures several times, the high molecular compound can be collected.

According to the present embodiment of the invention, in the titration measurement of high molecular compound and low molecular compound, the circular dichroism spectroscopy, Raman measurement, electrical conductivity measurement, PH measurement and absorbance measurement can proceed concurrently with the NMR measurement. By measuring the circular dichroism spectrum and Raman spectrum directly reflecting the molecular motion and molecular structure concurrently with measurement of the NMR spectrum reflecting a magnetic resonance of a nuclear spin, the relation between the structure change and chemical function of the high molecular compound can be measured directly. Further, by monitoring the low molecular compound solution constantly, the concentration controllability can be improved and the reduction in measurement procedures can be achieved.

Embodiment 2

In the embodiment described above, the measurement procedure has been explained in which the concentration of the high molecular compound is kept to be constant and the concentration of the low molecular compound is changed freely. In the present embodiment, procedures for measuring a high molecular compound under a predetermined condition of a low molecular compound solution by using the NMR measurement apparatus shown in connection with embodiment 1 will be described below with reference to the accompanying drawings.

Figure 4:
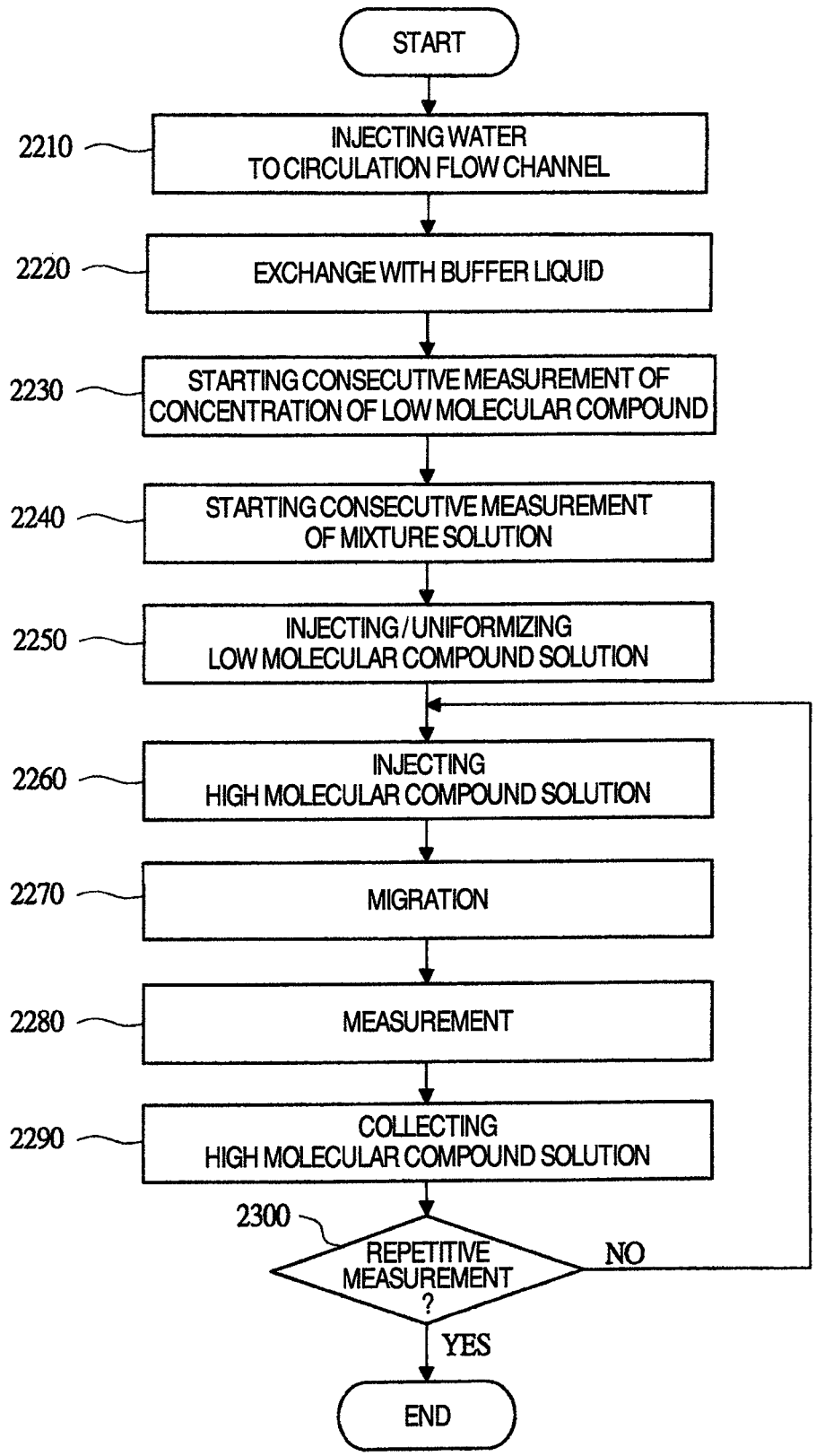
FIG. 4 is a flowchart of another embodiment of measurement in the NMR measurement apparatus according to the FIG. 1 embodiment of the invention.

The whole of titration measurement includes the following procedures as outlined in a flowchart of FIG. 4. Firstly, step 2210 of injecting water to the circulation channel and step 2220 of exchange with a buffer liquid are conducted and the whole circulation channel is filled up with a solution. Next, step 2230 of starting consecutive measurement of the concentration of a low molecular compound and step 2240 of starting consecutive measurement of a mixture solution are carried out. Then, step 2250 of injecting/uniformizing a low molecular compound solution is conducted to make uniform the concentration in the circulation channel inclusive of the reservoir. Thereafter, step 2260 of injecting the high molecular compound, step 2270 of migration, step 2280 of measurement and step 2290 of collecting the high molecular compound are carried out repetitively. It is to be noted that after completion of the measurement, cleaning with pure water is taken.

The step 2210 of water injection, step 2220 of exchange with buffer liquid, step 2230 of starting consecutive measurement of the low molecular compound concentration and step 2240 of starting consecutive measurement of mixture solution are similar to the steps 2010, 2020, 2030 and 2040 explained in connection with the previous embodiment 1 and will not be detailed herein. And step 2250 of injecting/uniformizing the low molecular compound solution and ensuing steps will be described below.

(Step 2250 of Injecting/Uniformizing Low Molecular Compound Solution)

Firstly, the circulating pump 100 is driven to start solution circulation. Then, by using the low molecular compound injection syringe 80 provided for the low molecular compound solution injecting unit 30, the low molecular compound solution is injected to the circulation channel. When the value of the third concentration meter 304 for low molecular compound converges to a constant value or falls within a constant range of fluctuations, the low molecular compound concentration in the circulation channel is determined to be uniform. As the concentration of the low molecular compound reaches a target concentration, the circulation is stopped.

If the low molecular compound concentration is lower than the target concentration, the process for injecting the low molecular compound solution is conducted to increase the concentration. If the low molecular compound concentration is higher than the target concentration, a solution not containing the low molecular compound is injected from the buffer liquid injection syringe 82 provided for the low molecular compound solution injecting unit 30, thus uniformizing the concentration through circulation to adjust the low molecular compound concentration.

In case the concentration of hydrogen ion is to be adjusted, the pH meter is arranged in place of the third concentration meter 304, an acid solvent and an alkaline solvent are set in the low molecular compound solution injection syringe 80 and buffer liquid injection syringe 82, respectively, and the pH value is adjusted through the unification process based on the solution injection and circulation.

(Step 2260 of Injecting High Molecular Compound Solution)

Circulation by the circulating pump 100 is executed and the flow path of first valve 72 is transferred to the sample solution injection syringe 90. Then, the high molecular compound is injected from the injection syringe 90 attached to the first valve 72.

(Step 2270 of Causing High Molecular Compound to Migrate)

The high molecular compound solution migrates along the flow of the low molecular compound solution to the mixing filter 32, first sample conveyance pipe 1602 and reservoir 10. During this period, the absorbance the first concentration meter 300 provided for the first sample conveyance pipe 1602 exhibits changes. As the absorbance of the second concentration meter 302 provided for the second sample conveyance pipe 1600 changes subsequently, the solution circulation is stopped. At that time, the high molecular compound exists in the reservoir 10.

(Step 2280 of Measurement)

A measurement is conducted with the solution being in stop. The measurement referred to herein includes, in addition to the NMR measurement, measurements by means of the different measuring instrument 310 provided for the first or second sample conveyance pipe (absorbance meter, circular dichroism spectrometer, Raman spectrometer or electrical conductivity meter).

(Step 2290 of Collecting High Molecular Compound Solution)

The solution circulation is started. When the values of first and second concentration meters 300 and 302 return to a value similar to that of the low molecular compound solution alone, the sample solution collection syringe 92 is driven to cause the high molecular compound to migrate from the separation filter 34 to the sample solution collection syringe 92 and to be collected thereby.

Although the low molecular compound mixes in the high molecular compound solution during collection, it is easy for the worker in this field of art to perform separation between the high molecular compound and the low molecular compound by using such a separating method as ultrafiltration generally known in chemistry and biochemical fields.

(Step 2300 of Repetitive Measurement)

By repeating the above four procedures of the step 2260 of injecting high molecular compound solution, step 2270 of causing high molecular compound to migrate, step 2280 of measurement and step 2290 of collecting the high molecular compound solution, a plurality of high molecular compounds can be measured easily under the constant condition of low molecular compound solution.

With the NMR measurement apparatus in the present embodiment as above, the concentration controllability can be improved through the circulation flow scheme in which the amount of the low molecular compound (second compound) relative to the high molecular compound (first compound) representing a measuring target can be changed by the concentration of the low molecular compound solution.

Embodiment 3

The foregoing embodiment 1 has been described as using the magnet of split type to apply a magnetic field to a sample in the NMR measurement apparatus capable of performing measurements concurrently with NMR measurement and improving the concentration control in the titration measurement utilizing sample solution adjustment based on the circulation flow scheme but the present embodiment will be described by way of application of a vertical integral type magnet. Configuration similar to that in the NMR measurement apparatus shown in connection with embodiment 1 will not be described.

Figure 5:
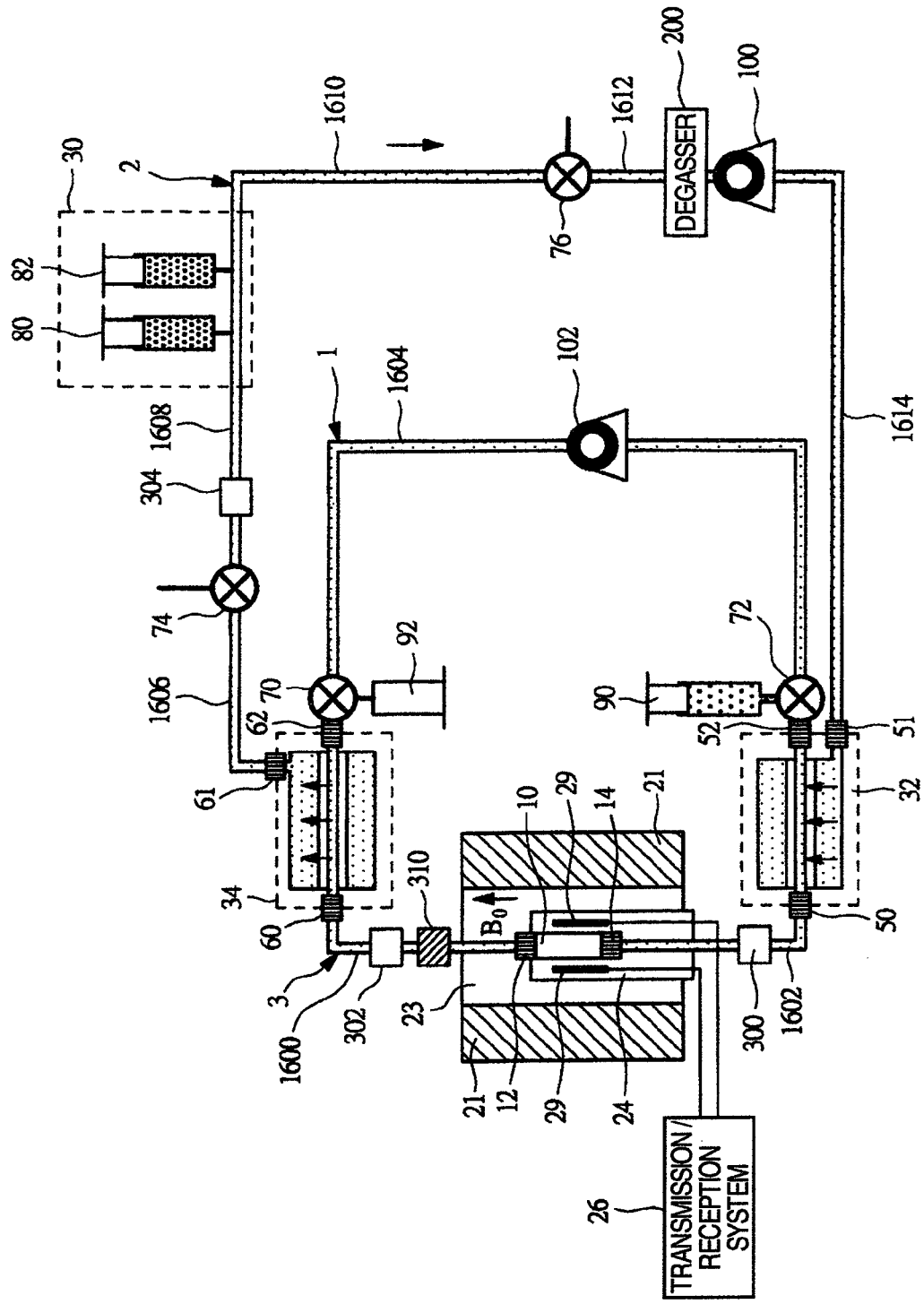
FIG. 5 is a diagram schematically illustrative of the construction of an NMR measurement apparatus according to another embodiment of the invention.

Referring to FIG. 5, a first sample conveyance pipe 1602 and a second sample conveyance pipe 1600 are so arranged as to pass through an NMR probe 24 placed in a space 23 inside a vertical integral type magnet 21. A reservoir 10 is disposed internally of a coil 29 inside the probe at a location suitable for observation of NMR signals. The proper positional relation differs depending on the structure of the probe and the coil shape but a location where the detected NMR signal is maximized is preferable.

An injection port 14 is provided at the bottom of the reservoir 10 and the injection port 14 is connected with the first sample conveyance pipe 1602. Also, a drainage port 12 is provided at the top of the reservoir 10 and is connected with the second sample conveyance pipe 1600. With this configuration, like the measuring methods shown in the embodiments 1 and 2, NMR measurement based on titration measurement using the constant amount of high molecular compound can also be conducted concurrently with measurements by other measuring instruments in the case of the integral type magnet.

As will be seen from the above, in the NMR measurement apparatus according to the present embodiment, the concentration controllability can be improved in the circulation flow scheme in which the amount of the second compound (for example, low molecular compound) relative to the first compound (for example, high molecular compound) representing a measuring target is changed by the concentration of a solution of the second compound.

Embodiment 4

In connection with the above embodiment 3, an instance has been described where in the NMR measurement apparatus capable of performing measurements concurrently with the NMR measurement and improving the concentration controllability in the titration measurement utilizing the sample solution adjustment based on the circulation flow scheme of the present invention but in the present embodiment, application of another type of NMR probe will be described. Configuration similar to that in the NMR measurement apparatus shown in connection with embodiment 3 will not be described.

Figure 6:
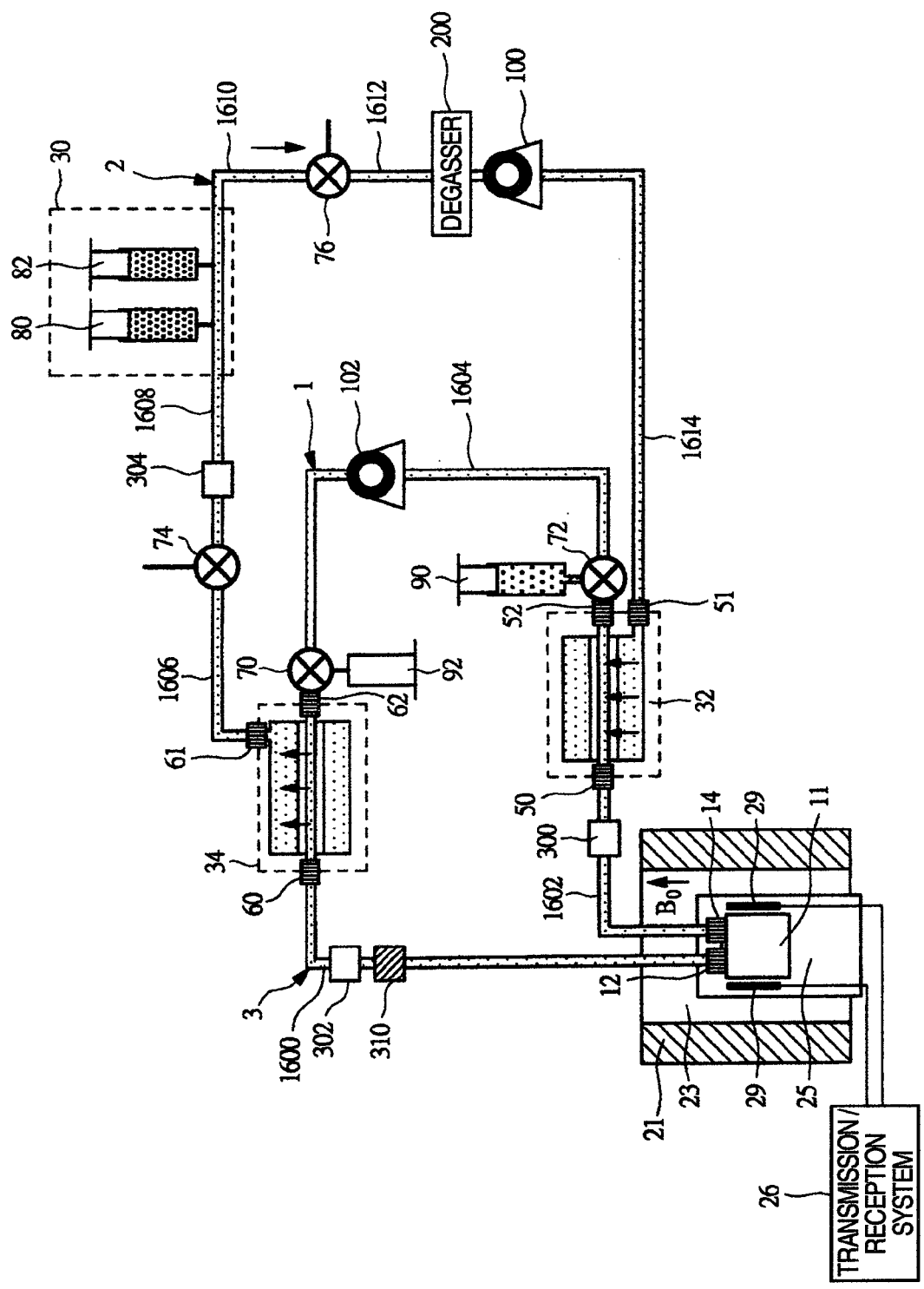
FIG. 6 is a diagram schematically illustrative of the construction of an NMR measurement apparatus according to still another embodiment of the invention.
Figure 7:
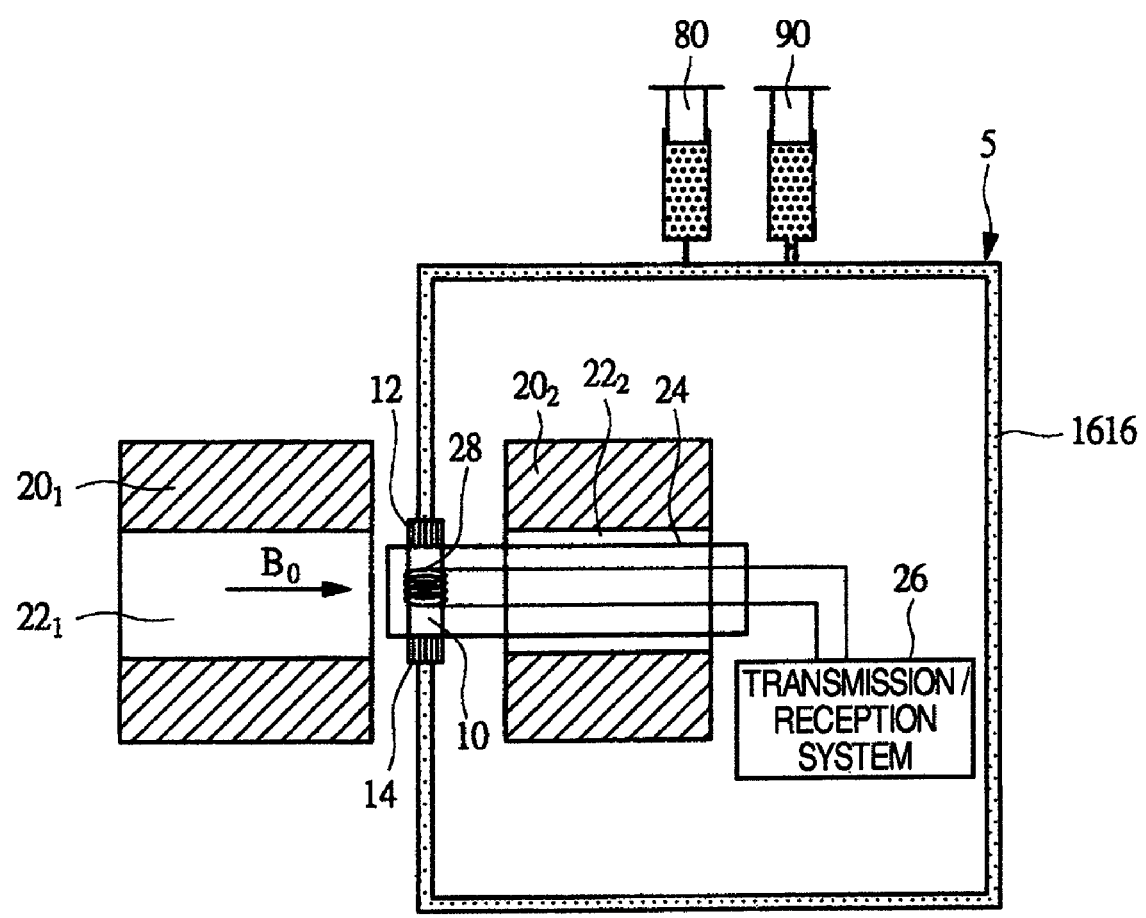
FIG. 7 is a diagram schematically illustrative of the construction of an NMR measurement apparatus the present inventors have studied.

Turning to FIG. 6, a reservoir 11 is disposed internally of an NMR probe 25 placed in a space 23 inside a vertical integral type magnet 21. The reservoir 11 is set at a location suitable for cooperating with a coil 29 inside the probe to observe NMR signals. The proper positional relation differs depending on the structure of the probe and the coil shape but a location where the detected NMR signal is maximized is preferable.

An injection port 14 and a drainage port 12 are provided at the top of reservoir 11. The injection port 14 is connected to a first sample conveyance pipe 1602. The drainage port 12 is connected with a second sample conveyance pipe 1600. Both the first and second sample conveyance pipes 1602 and 1600 jut out of the top of the NMR probe 25 and pass through a space 23 so as to be connected to a mixing filter 32 and a separation filter 34, respectively, above the magnet 21. With this configuration, even when the NMR probe of not flow-through type or thin-pipe unpenetrated type, either, is used in the integral magnet, like the measuring methods shown in the embodiments 1 and 2, NMR measurement based on titration measurement using the constant amount of high molecular compound can also be conducted concurrently with measurements by other measuring instruments.

As will be seen from the above, in the NMR measurement apparatus according to the present embodiment, the concentration controllability can be improved in the circulation flow scheme in which the amount of the second compound (for example, low molecular compound) relative to the first compound (for example, high molecular compound) representing a measuring target is changed by the concentration of a solution of the second compound.

While in the foregoing the invention made by the present inventors has been described specifically on the basis of the embodiments, the present invention is in no way limited to the foregoing embodiments and can be modified or altered in various ways without departing from the gist thereof.

For example, the foregoing embodiments have been described as being applied to the NMR measurement apparatus using the circulation flow scheme but the present invention can also be applicable to a titration measurement apparatus using the circulation flow scheme.

The present invention is concerned with the NMR measurement apparatus and the measuring technology using the same and especially it can be utilized widely for manufactures of the NMR measurement apparatus which executes NMR measurements of high molecular compound such as protein.

By applying the present invention to the high molecular compound typified by protein functional in the living body, the constant volume of a sample can be kept irrespective of the titration condition through the use of a constant amount of the high molecular compound and besides, the NMR measurement for which the solution condition is changed and other kinds of measurements can be executed concurrently and repetitively, so that the efficiency of analysis of a biochemical process taking place in the living body can be improved in the field of life science, leading to highly efficient disease mechanism analysis and screening based on the measurement of the intensity of bonding with a disease related protein in the field of medical care and pharmacology.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A nuclear magnetic resonance measurement apparatus comprising:
    a reservoir for holding a mixture solution containing a first compound and a second compound of lower molecular weight than that of the first compound;
    a magnet for applying a magnetic field to said mixture solution held in said reservoir;
    a nuclear magnetic resonance probe attached to said reservoir;
    a mixing filter for mixing a first solution containing said first compound and a second solution containing said second compound and draining a resultant solution as said mixture solution;
    a separation filter for performing separation between said first solution and said second solution from said mixture solution injected thereto; and
    pipes for constituting a first flow channel through which said first solution drained out of said separation filter is injected to said mixing filter, a second flow channel through which said second solution drained out of said separation filter is injected to said mixing filter and a third flow channel through which said mixture solution drained out of said mixing filter is injected to said separation filter by way of said reservoir.

2. A nuclear magnetic resonance measurement apparatus according to claim 1 further comprising:
an injecting unit provided for said second flow channel and adapted to inject said second solution in which said second compound is adjusted to a predetermined concentration; and
a first pump provided for said second flow channel and adapted to circulate said second solution to said second and third flow channels.

3. A nuclear magnetic resonance measurement apparatus according to claim 1 further comprising:
a first concentration meter provided for said third flow channel laid between an injection port of said reservoir and a drainage port of said mixing filter;
a second concentration meter provided for said third flow channel laid between a drainage port of said reservoir and an injection port of said separation filter;
a third concentration meter provided for said second flow channel; and
a computer connected to said nuclear magnetic resonance probe and said first to third concentration meters,
wherein said computer has the function to control
(a) step of circulating a buffer liquid through said first to third flow channels,
(b) step of starting, after the step (a), measurements by said first to third concentration meters,
(c) step of injecting, after the step (b), said first solution to said first flow channel, circulating said first solution through said first and third flow channels and causing said first and second concentration meters to measure a uniform concentration state of said first solution,
(d) step of injecting, after the step (c), said second solution to said second flow channel, circulating said second solution through said second and third flow channels and causing said third concentration meter to measure a uniform concentration state of said second solution,
(e) step of measuring, after the step (d), nuclear magnetic resonance of said mixture solution by means of said nuclear magnetic resonance probe, and
(f) step of changing, after the step (e), the concentration of said second solution and performing said steps (d) and (e) repetitively.

4. A nuclear magnetic resonance measurement apparatus according to claim 1, wherein said reservoir has an injection port to which said mixture solution is injected and a drainage port from which said mixture solution is drained, said mixing filter has a first injection port to which said first solution is injected, a second injection port to which said second solution is injected and a drainage port from which said mixture solution is drained, said separation filter has an injection port to which said mixture solution is injected, a first drainage port from which said first solution is drained and a second drainage port from which said second solution is drained,
said apparatus further comprising:
a first sample conveyance pipe connected with the injection port of said reservoir and the drainage port of said mixing filter and constituting said third flow channel;
a second sample conveyance pipe connected with the drainage port of said reservoir and the injection port of said separation filter and constituting said third flow channel;
a first valve connected to the first injection port of said mixing filter;
a second valve connected to the first drainage port of said separation filter;
a third sample conveyance pipe connected with one entrance of said first valve and one entrance of said second valve and constituting said first flow channel;
a fourth sample conveyance pipe connected to the second drainage port of said separation filter and constituting said second flow channel;
a drainage valve connected to said fourth sample conveyance pipe;
a fifth sample conveyance pipe connected to said drainage valve and constituting said second flow channel;
an injecting unit connected to said fifth sample conveyance pipe to inject said second solution;
a sixth sample conveyance pipe connected to said injecting unit and constituting said second flow channel;
a water injection valve connected to said sixth sample conveyance pipe;
a seventh sample conveyance pipe connected to said water injection valve and constituting said second flow channel;
a first pump connected to said seventh sample conveyance pipe and adapted to circulate said second solution; and
an eighth sample conveyance pipe connected with said first pump and said second injection port of said mixing filter and constituting said second flow channel.

5. A nuclear magnetic resonance measurement apparatus according to claim 4, wherein said third flow channel is connected with at least one of a Raman spectrometer, a circular dichroism spectrum meter, an absorbance meter, and an electrical conductivity meter.

6. A nuclear magnetic resonance measurement apparatus according to claim 4, wherein said first flow channel is provided with a second pump for circulating said first solution.

7. A nuclear magnetic resonance measurement apparatus according to claim 4, wherein each of said mixing filter and said separation filter has a hollow filter member capable of passing only said second solution therethrough.

8. A nuclear magnetic resonance measurement apparatus according to claim 4, wherein a first concentration meter or a first hydrogen ion concentration meter is provided for said third flow channel laid between the injection port of said reservoir and the drainage port of said mixing filter, a second concentration meter or a second hydrogen ion concentration meter is provided for said third flow channel laid between the drainage port of said reservoir and the injection port of said separation filter, and a third concentration meter or a third hydrogen ion concentration meter is provided for said second flow channel.

9. A nuclear magnetic resonance measurement apparatus according to claim 8, wherein each of said first to third concentration meters or each of said first to third hydrogen ion concentration meters functions to display or record a set of measurement-executed time and measured data in each measurement or to transfer data.

10. A nuclear magnetic resonance measurement apparatus according to claim 4, wherein said injecting unit has a first syringe to which a solution containing said second compound is injected and a second syringe to which a solution not containing said second compound is injected.

11. A nuclear magnetic resonance measurement apparatus according to claim 4, wherein said first valve is attached with a third syringe for injection of said first solution and said second valve is attached with a fourth syringe for collection of said first solution.

12. A measuring method using a nuclear magnetic resonance measurement apparatus having:

a reservoir for holding a mixture solution containing a first compound and a second compound of lower molecular weight than that of the first compound;

a magnet for applying a magnetic field to said mixture solution held in said reservoir;

a nuclear magnetic resonance probe attached to said reservoir;

a mixing filter for mixing a first solution containing said first compound and a second solution containing said second compound;

a separation filter for performing separation between said first solution and said second solution;

a first flow channel through which said first solution drained out of said separation filter is injected to said mixing filter;

a second flow channel through which said second solution drained out of said separation filter is injected to said mixing filter; and a third flow channel through which said mixture solution drained out of said mixing filter is injected to said separation filter by way of said reservoir, wherein a first concentration meter is provided for said third flow channel laid between an injection port of said reservoir and a drainage port of said mixing filter, a second concentration meter is provided for said third flow channel laid between a drainage port of said reservoir and an injection port of said separation filter, and a third concentration meter is provided for said second flow channel, said measuring method comprising the steps of:

(a) circulating a buffer liquid through said first to third flow channels;

(b) starting, after the step (a), measurements by said first to third concentration meters;

(c) injecting, after the step (b), said first solution to said first flow channel, circulating said first solution through said first and third flow channels and causing said first and second concentration meters to measure a uniform concentration state of said first solution;

(d) injecting, after the step (c), said second solution to said second flow channel, circulating said second solution through said second and third flow channels and causing said third concentration meter to measure a uniform concentration state of said second solution;

(e) measuring, after the step (d), nuclear magnetic resonance of said mixture solution by means of said nuclear magnetic resonance probe; and (f) changing, after the step (e), the concentration of said second solution and performing said steps (d) and (e) repetitively.

13. A measuring method using the nuclear magnetic resonance measurement apparatus according to claim 12, wherein the concentration of said second compound is measured consecutively by using said third concentration meter to record or display a set of measurement-executed time and measured data in each measurement or to transfer data.

14. A measuring method using the nuclear magnetic resonance measurement apparatus according to claim 12, wherein in said step (e), said first and second concentration meters are used to perform consecutive measurement of an absorbance value of said mixture solution, a set of measurement-executed time and measured data in each measurement is recorded or displayed or data is transferred and besides the nuclear magnetic resonance of said mixture solution is measured.

15. A measuring method using the nuclear magnetic resonance measurement apparatus according to claim 12, wherein in said step (e), changes in solution state are monitored consecutively during the circulation by means of said first and second concentration meters, the concentration of said first compound in said mixture solution is determined as being uniform when the values of said first and second concentration meters become equal to each other and fluctuate with time substantially equally and thereafter the nuclear magnetic resonance of said mixture solution is measured.

16. A measuring method using the nuclear magnetic resonance apparatus according to claim 12, wherein in said step (d), the concentration of said second compound in said second and third flow channels is determined to be uniform when the value of said third concentration meter is converged to a constant value or to a constant range of fluctuations, whereby if the concentration of said second compound is lower than a target concentration, said second solution is injected to increase the concentration or if the concentration of said second compound is higher than the target concentration, a solution not containing said second compound is injected to decrease the concentration and when the concentration of said second compound reaches the target concentration, the circulation is stopped, in said step (e), the nuclear magnetic resonance measurement is started, and in said step (f), for all concentration conditions of said second compound, the concentration of said second compound is adjusted and the nuclear magnetic resonance measurement is repeated.

17. A measuring method using the nuclear magnetic resonance measurement apparatus according to claim 12, wherein concurrently with the nuclear magnetic resonance measurement in said step (e), measurement with the help of at least one of the absorbance meter, circular dichroism spectrometer, Raman spectrometer and electrical conductivity meter which are provided for said third flow channel is conducted.

18. A measuring method using the nuclear magnetic resonance measurement apparatus according to claim 17, pieces of data obtained through the measurement by said nuclear magnetic resonance probe, measurement by said first to third concentration meters, measurement by said circular dichroism spectrometer and measurement by said Raman spectrometer are displayed or recorded or subjected to data transfer and the pieces of data can be referred to and compared with one another.

19. A measuring method using the nuclear magnetic resonance measurement apparatus according to claim 12, further comprising the steps of:

(g) closing, after said step (f), said first flow channel and making circulation through said second and third flow channels to collect said first compound between said separation filter and said first flow channel and collecting a solution containing said first compound from a path between said separation filter and said first flow channel when values of said first and second concentration meters approach a value in the absence of said first compound;

(h) opening, after said step (g), said first flow channel and circulating said first solution through said first and third flow channels; and (i) repeating, after said step (h), said steps (g) and (h) when the values of said first and second concentration meters again fluctuate.

20. A measuring method using a nuclear magnetic resonance measurement apparatus having:

a reservoir for holding a mixture solution containing a first compound and a second compound of lower molecular weight than that of the first compound;

a magnet for applying a magnetic field to said mixture solution held in said reservoir;

a nuclear magnetic resonance probe attached to said reservoir;

a mixing filter for mixing a first solution containing said first compound and a second solution containing said second compound;

a separation filter for performing separation between said first solution and said second solution;

a first flow channel through which said first solution drained out of said separation filter is injected to said mixing filter;

a second flow channel through which said second solution drained out of said separation filter is injected to said mixing filter; and a third flow channel through which said mixture solution drained out of said mixing filter is injected to said separation filter by way of said reservoir, wherein a first concentration meter is provided for said third flow channel laid between an injection port of said reservoir and a drainage port of said mixing filter, a second concentration meter is provided for said third flow channel laid between a drainage port of said reservoir and an injection port of said separation filter, and a third concentration meter is provided for said second flow channel, said measuring method comprising the steps of:

(a) circulating a buffer liquid through said first to third flow channels;

(b) starting, after the step (a), measurements by said first to third concentration meters;

(c) injecting, after the step (b), said second solution to said second flow channel, circulating said second solution through said second and third flow channels and causing said third concentration meter to measure a uniform concentration state of said second solution;

(d) injecting, after the step (c), said first solution to said first flow channel, circulating said first solution through said first and third flow channels and causing said first and second concentration meters to measure a uniform concentration state of said mixture solution;

(e) measuring, after the step (d), nuclear magnetic resonance of said mixture solution by means of said nuclear magnetic resonance probe; and (f) changing, after the step (e), the concentration of said second solution and performing said steps (d) and (e) repetitively.

* * * * *